US009066658B2

(12) United States Patent
Hamel et al.

(10) Patent No.: US 9,066,658 B2
(45) Date of Patent: Jun. 30, 2015

(54) METHOD AND SYSTEM FOR VIDEO BASED IMAGE DETECTION/IDENTIFICATION ANALYSIS FOR FLUID AND VISUALIZATION CONTROL

(75) Inventors: Andrew Hamel, San Mateo, CA (US); Brannon P. Wells, San Jose, CA (US); Ruzbeh Shariff, Santa Clara, CA (US)

(73) Assignee: STRYKER CORPORATION, Kalamazoo, MI (US)

( * ) Notice: Subject to any disclaimer, the term of this patent is extended or adjusted under 35 U.S.C. 154(b) by 362 days.

(21) Appl. No.: 12/932,793

(22) Filed: Mar. 7, 2011

(65) Prior Publication Data
US 2011/0237880 A1 Sep. 29, 2011

Related U.S. Application Data

(60) Provisional application No. 61/340,805, filed on Mar. 23, 2010.

(51) Int. Cl.
*A61B 1/04* (2006.01)
*A61B 1/015* (2006.01)
*A61B 1/00* (2006.01)
*A61B 1/045* (2006.01)
(Continued)

(52) U.S. Cl.
CPC .............. *A61B 1/015* (2013.01); *A61B 1/00009* (2013.01); *A61B 1/045* (2013.01); *A61B 1/126* (2013.01); *A61B 1/3132* (2013.01); *A61B 17/32002* (2013.01); *A61B 18/1482* (2013.01); *A61B 2017/00296* (2013.01); *A61B 2018/00773* (2013.01); *A61B 2018/00863* (2013.01); *A61B 2218/001* (2013.01); *G06F 19/3437* (2013.01)

(58) Field of Classification Search
CPC ...... A61B 1/3132; A61B 1/317; A61B 1/015; A61B 1/00009; A61B 2018/00773; A61B 2018/00702; A61M 1/0058; A61M 2205/381; A61M 2205/3313
USPC .................. 600/103, 117, 118, 157, 158, 159
See application file for complete search history.

(56) References Cited

U.S. PATENT DOCUMENTS 4,858,164 A * 8/1989 Schildhorn .................... 708/520
5,187,572 A * 2/1993 Nakamura et al. ............. 348/68
(Continued)

FOREIGN PATENT DOCUMENTS

WO  WO 2009/105488 A2   8/2009

OTHER PUBLICATIONS

European Office Action issued in corresponding European Patent Appln. No. 11 159 096.4 dated Aug. 2, 2012 (4 sheets).
(Continued)

*Primary Examiner* — John P Leubecker
(74) *Attorney, Agent, or Firm* — Flynn, Thiel, Boutell & Tanis, P.C.

(57) ABSTRACT

In a surgical system, a system controller executes a video signature identification and image control routine to maintain quality of a video image taken by a video camera located at a surgical site and provided on a video display. The system includes a video camera/light source handpiece for insertion into a patient body. A tool is inserted separately into the surgical site. Fluid input into the surgical site is provided by a liquid pump or by an insufflator. Video signals are analyzed and fluid input/output, fluid pressure, and/or tool operation is automatically controlled to maintain image quality of the surgical site without manual adjustments.

21 Claims, 10 Drawing Sheets

(51) Int. Cl.
*G06F 19/00* (2011.01)
*A61B 1/12* (2006.01)
*A61B 1/313* (2006.01)
*A61B 17/32* (2006.01)
*A61B 18/14* (2006.01)
*A61B 17/00* (2006.01)
*A61B 18/00* (2006.01)

(56) References Cited

U.S. PATENT DOCUMENTS

| | | | | |
|---|---|---|---|---|
| 5,318,516 A | * | 6/1994 | Cosmescu | 604/35 |
| 5,343,855 A | * | 9/1994 | Iida et al. | 600/157 |
| 5,451,222 A | * | 9/1995 | De Maagd et al. | 606/41 |
| 5,685,821 A | * | 11/1997 | Pike | 600/118 |
| 6,015,406 A | * | 1/2000 | Goble et al. | 606/41 |
| 6,024,720 A | * | 2/2000 | Chandler et al. | 604/35 |
| 6,178,346 B1 | * | 1/2001 | Amundson et al. | 600/473 |
| 6,447,446 B1 | * | 9/2002 | Smith et al. | 600/157 |
| 6,889,075 B2 | * | 5/2005 | Marchitto et al. | 600/473 |
| 7,479,106 B2 | * | 1/2009 | Banik et al. | 600/159 |
| 7,981,073 B2 | * | 7/2011 | Mollstam et al. | 604/28 |
| 8,231,523 B2 | * | 7/2012 | Uesugi et al. | 600/118 |
| 2001/0031976 A1 | | 10/2001 | Lobdell | |
| 2004/0133149 A1 | * | 7/2004 | Haischmann et al. | 604/31 |
| 2005/0171470 A1 | * | 8/2005 | Kucklick et al. | 604/96.01 |
| 2005/0182296 A1 | * | 8/2005 | Furukawa | 600/118 |
| 2005/0228231 A1 | | 10/2005 | Mackinnon et al. | |
| 2005/0256370 A1 | * | 11/2005 | Fujita | 600/101 |
| 2007/0255107 A1 | * | 11/2007 | Kawanishi | 600/159 |
| 2008/0243054 A1 | * | 10/2008 | Mollstam et al. | 604/31 |
| 2009/0227999 A1 | | 9/2009 | Willis et al. | |
| 2010/0130836 A1 | * | 5/2010 | Malchano et al. | 600/301 |
| 2012/0071720 A1 | * | 3/2012 | Banik et al. | 600/118 |

OTHER PUBLICATIONS

European Search Report, dated Jul. 25, 2011 (7 sheets).
European Patent Office Communication dated May 29, 2013 (5 pages).

* cited by examiner

METHOD AND SYSTEM FOR VIDEO BASED IMAGE DETECTION/IDENTIFICATION ANALYSIS FOR FLUID AND VISUALIZATION CONTROL

CROSS REFERENCE TO RELATED APPLICATION

This application claims the benefit of U.S. Provisional Application No. 61/340,805, filed Mar. 23, 2010, the disclosure of which is incorporated herein by reference in its entirety.

FIELD OF THE INVENTION

This invention is directed to a method and system for analyzing video images to obtain an acceptable image of a surgical site for display and use in a surgical procedure.

BACKGROUND OF THE INVENTION

In a typical arthroscopic surgical procedure, fluid is pumped into a surgical field to create a positive pressure in a joint to provide space to perform the procedure and to reduce bleeding by creating a tamponade effect. Fluid is pumped into and out of the joint to remove debris and blood from the surgical site. A video sensing device typically provides images of the surgical site. A surgeon manually controls the inflow and outflow of fluid from the surgical site to prevent debris, blood or other particulates from degrading the image that is necessary to perform the procedure. This manual task can be difficult and lead to additional time for conducting a surgery and potentially compromise the surgery if the images are not acceptable.

Prior art U.S. Patent Pub. No. 2008/0243054 A1 discloses a known arrangement, as shown in prior art FIG. 1, for detecting and distinguishing blood and debris disposed within a shoulder joint during an arthroscopic procedure. The pressure in the shoulder joint, and the liquid flow from an irrigation system, is controlled to attempt to provide good viewing with the arthroscope by keeping video camera images free from blood and debris.

In prior art FIG. 1, the arrangement includes an operating control device 17 and a saline bag 10 connected to a liquid inflow pump 2 that pressurizes feed tubing 13. The arrangement includes a pressure sensor 5 joined to the feed tubing 13. The feed tubing 13 connects to an arthroscope 14 that includes a video camera 22. A shaver 15 connects to an outflow tubing 16 that is in fluid communication with an outflow pump 3. During flow, the pressure drops all the way from the inflow liquid pump 2 to the outflow pump 3. In prior art FIG. 1, a video signal processor 23 is shown adjacent the operating control device 17.

In prior art FIG. 1, the detection of hemoglobin is obtained by use of light reflected from the hemoglobin in blood disposed in the joint 1. The light reflected is that which is radiated by a light source (not illustrated) known in the art of endoscopy. The light is introduced in a designated channel in the arthroscope 14 that is placed in the shoulder. The reflection of white light is detected by the video camera 22, which is fitted on the arthroscope 14. The video signal that is output from the video camera 22 is provided to a video signal processor 23.

The video signal is composed of separate red, blue and green video signal components that, in combination, compose the video color information. The video signal from the camera 22 is fed to the signal processor 23 that divides every video line signal into 0.64 microsecond time slots. This arrangement corresponds to 100 time slots for every video signal line, where a picture frame is made up of 625 lines (PAL). The signal levels of red, blue and green are nearly the same for the images common in the view field of the arthroscope, meaning that it is generally ranging from white to black. If the signal level of red is >20% of either the blue or green during a time slot, a score of one is registered in a first frame memory in the signal processor 23. If the whole image is red, 62,500 score points would be registered. Every picture frame has its own score. The first frame memory in the signal processor 23 has a rolling register function that has the capacity of scoring points from 10 frames. The frame memory is updated as every frame is completed and delivered by the camera. At every new frame, the score value of the oldest frame is discarded. A score sum for the ten frames is calculated every time a new frame is delivered by the camera, thus introducing an averaging function.

If, during a period of 10 frames, the score sum is >30,000, blood is considered present, and if the score sum is >70,000, much blood is considered present.

If the score sum is >30,000, the video signal processor 23 will signal to the operating control device 17 which will react by increasing the flow of the aspiration pump to a higher level to rinse the shoulder. This higher level is preselected in the menu of the pump system, and is in this case 300 ml/min. If the score sum is >70,000, the flow will increase to 450 ml/min. When the blood detection determines that the increased flow has rinsed the shoulder as the signal level has returned to a low level, the aspiration pump will return to the intrinsic flow of 150 ml/min after a timeout of 30 seconds. Also, to stop bleeding of a ruptured blood vessel in the shoulder joint 1, the pressure in the joint is increased by a pressure control for the same time that flow is elevated. This pressure increase is predetermined in menu settings of the pump, and is in this example 40 mm Hg. Also other picture analysis techniques as known in the art could be used.

To detect debris, the signal processor 23 divides every video frame into 128×128 pixel elements. Every such pixel has a signal level that corresponds to the whiteness of the object that is visualized by the camera. This whiteness is nearly the same from video image frame to video image frame. The signal processor stores a value from 0 to 15 as this intensity value of the video signal of each pixel in a second frame memory. The pixel values are stored in a matrix fashion. For each video image frame 25 consecutive frame matrixes are stored. The second memory in the signal processor has a rolling register function that rolls the 25 frames in a first in-first out fashion. The second memory is updated as every video image frame is completed and delivered by the camera. As a new frame is developed by the camera, the oldest frame is discarded. A variation in the pattern in the second stored matrix is detected by the signal processing unit. This variation is identified as pixel intensities that are recognized as moving from one adjacent pixel to another in an identifiable fashion. As every pixel has a location in the matrix that corresponds to the physical image, a movement of intensity in the matrix location from image frame to image frame is a movement in relation to the surrounding, of a single object, in this case debris that float in the shoulder joint. Movement can be in any direction in the matrix. If 10 such movements are detected during one frame, a first score value is incremented by one in a memory cell representing a first score value. This score value is incremented for each detection, and is decremented down to 0 for every frame there is no such detection. If there are over 500 detections in one frame, the camera is moved, and no score values are given. Also, other picture analysis techniques as known in the art could be used.

Every second a frame matrix is stored in a third frame memory. This memory also has a rolling register function that rolls the 25 frames in a first in-first out fashion. If predominant consistently low signal levels are occurring in the third frame memory, dark areas are identified. If these dark areas are elevated to a consistent signal >25% level over a time of 5 seconds, homogeneous debris is identified as being present in the shoulder joint. Such occurrence increases the value of a second score value by 10. If there is no such occurrence, this second score value will be decremented by 10 down to 0.

If either the first or second score values are >50, debris is considered present, and the video signal processor 23 will signal to the operating control device 17 which will react by increasing the flow of the aspiration pump to a higher level to rinse the shoulder. This higher level is preselected in the menu of the pump system, and is in this case 300 ml/min. When the debris detection determines that the increased flow has rinsed the shoulder as the score value has returned to <50, the aspiration pump will return to the intrinsic flow of 150 m./min after a timeout of 5 seconds, and both score values are reset.

The system described above, however, is limited to an operating control device 17 for a pump that only controls liquid inflow for the arthroscope 14 and liquid outflow from a separate shaver 15. In this system, there is no control of any functions other than the liquid inflow pump 2 and liquid outflow pump 3. Further, the prior art system is limited to processing red, blue and green video signal components. Finally, the FIG. 1 system is limited to controlling flow pressure/inflow and outflow rates in order to obtain a desired video image.

SUMMARY OF THE INVENTION

The present invention provides an enhanced video image for a surgical site by determining one or more of a plurality of conditions that degrade the quality of at least portions of the video image of a surgical site, and automatically selecting from a plurality of system control arrangements the optimal functions to be controlled in order to maximize the quality of the video image provided on a display for a surgeon during a medical procedure.

In one embodiment of the invention, a video based image detection/identification system for sensing fluid and for visualization control is provided with a surgical system including a cutting tool for manipulating tissue, a pump system for providing fluid, a light source, and a video sensing device for obtaining video signals of images at a surgical site for display. A system controller controls at least one of the cutting tool, the pump system, and the video sensing device to maintain image quality of the images obtained by the video sensing device for display. The controller receives and processes video signals from the video sensing device to determine video signatures that correspond to specific conditions at a surgical site that interfere with image quality. In response to an identified condition at the surgical site that degrades the video image, the controller controls the cutting tool, pump system, light source and/or video sensor device so that the images from the video signals return to an acceptable quality automatically, so as to free a user from the task of manually controlling the devices to maintain a desired video image. The video signatures determined by the controller include one or more of bubbles, debris and bleeders located at a surgical site as viewed by the video sensing device of an endoscopic system. Another video signature determined by the controller determines the presence of debris located at a distal tip of a housing of a handpiece associated with a video sensing device.

In one embodiment, the invention is provided with a laparoscopic system that utilizes an insufflator as a pump to provide gas to a surgical site. In this embodiment, the video signatures are provided to detect smoke, debris and other conditions.

In some embodiments, predetermined wavelengths of energy are provided from the light source to the surgical site. The energy for determining the conditions at the surgical site can be emitted at wavelengths that are out of the visible light range.

In response to the various video signatures, the system controller of one embodiment of the invention controls at least one of suction pressure, a suction valve position, input pressure, an input flow valve, color imaging processing of the camera control unit, light source intensity, and color balance of the video sensing device to improve the video image for display.

By directly comparing video images for quality and directly operating various devices in response to image quality issues, the invention operates as a closed system. More specifically, the quality of the image is not obtained or improved by sensing pressure values or other conditions that do not have a direct effect on the image. Instead, the controller acts as a closed system by receiving direct video information as to the quality of an image and then controlling devices to maintain image quality.

DETAILED DESCRIPTION OF THE INVENTION

Figure 1:
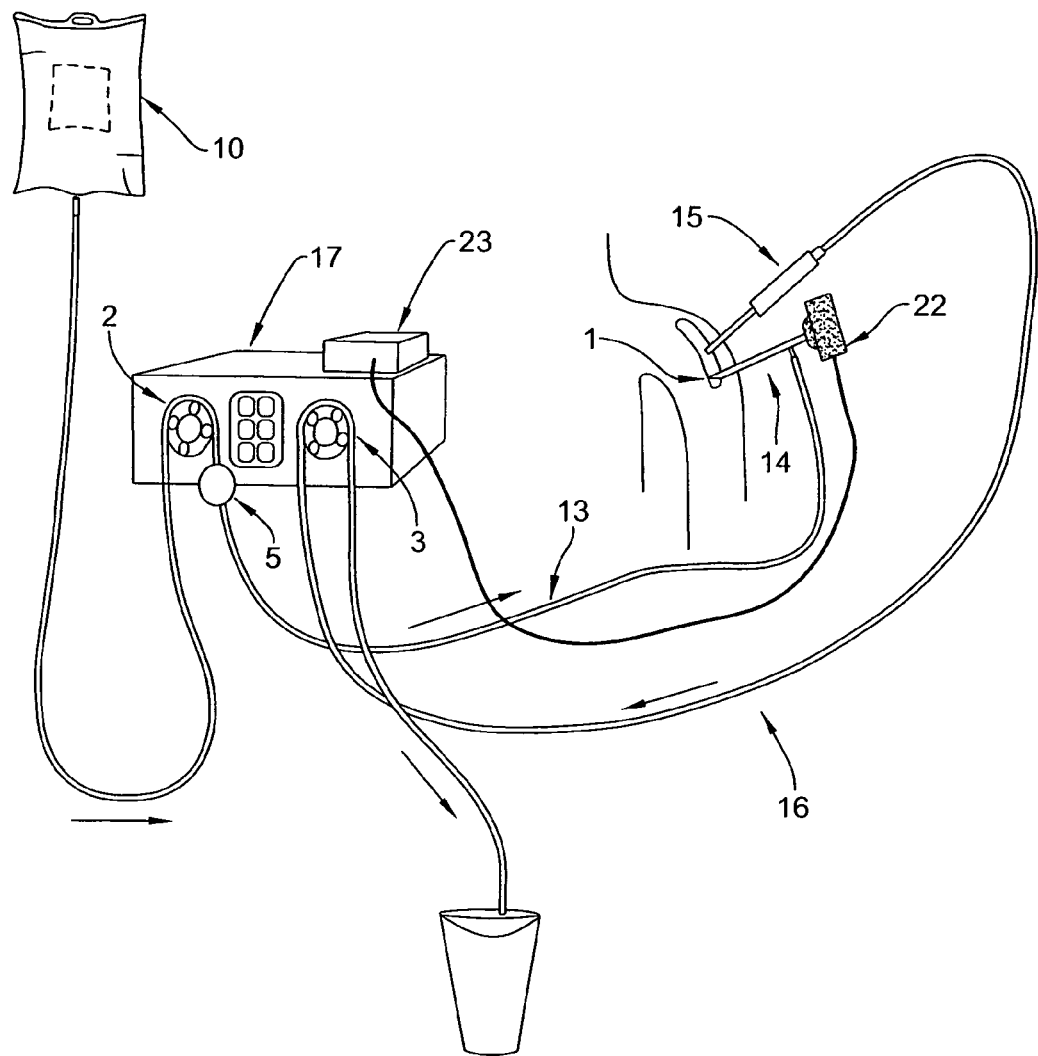
FIG. 1 depicts a prior art arthroscopic system.
Figure 2:
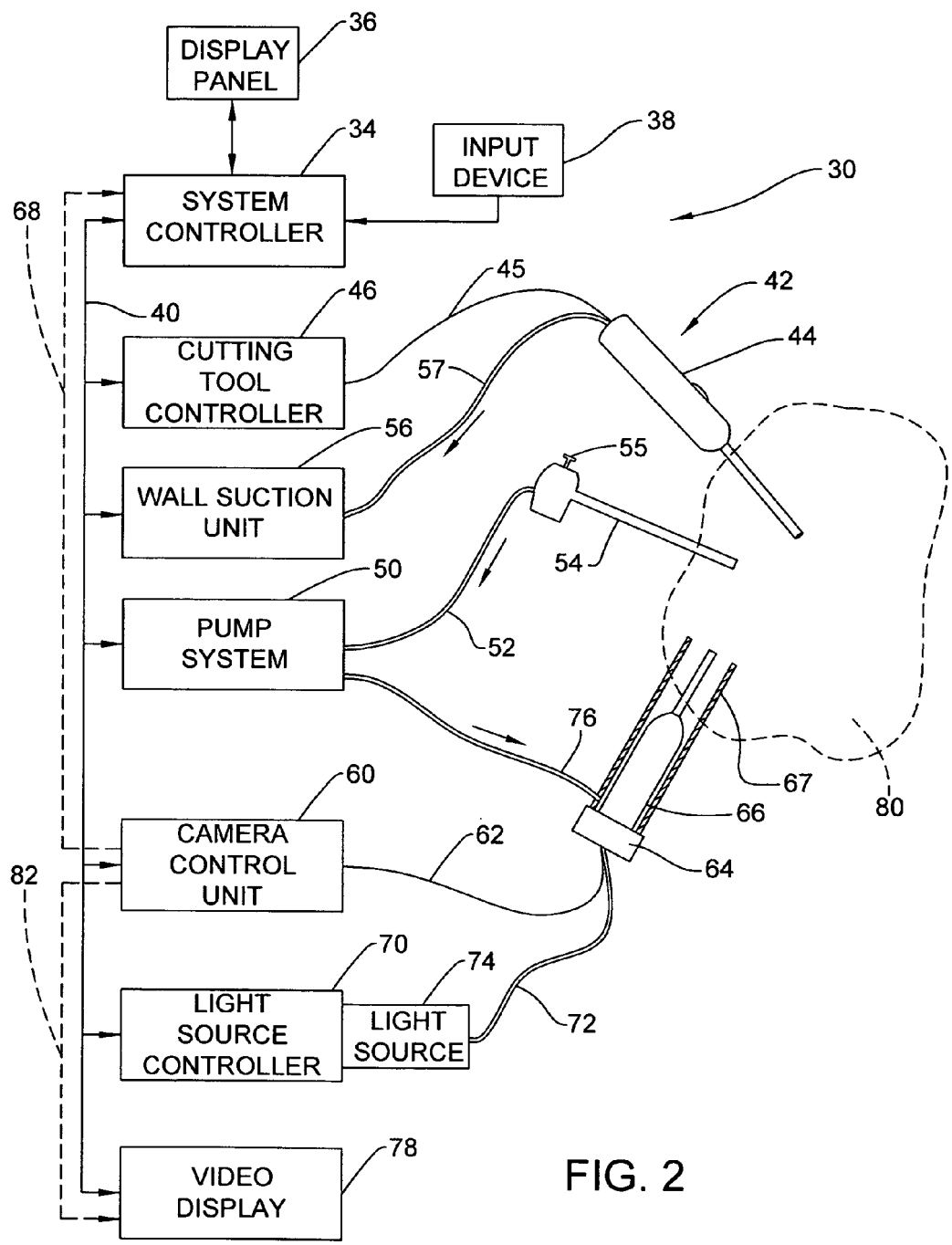
FIG. 2 depicts a block diagram of an integrated surgical control system, along with surgical tools disposed at a surgical site.

FIG. 2 illustrates an integrated surgical control system 30 that includes a system controller 34 having a display panel 36 and an input device 38. The system controller 34 is connected by a computer network 40 to communicate with a plurality of surgical devices. The devices may include a cutting tool 42, such as a surgical shaver, having a handpiece 44 connected by a signal line 45 to a cutting tool controller 46 that communicates with the system controller 34 over the network 40. The surgical control system 30 can be an arthroscopic surgical control system.

The surgical control system 30 includes a pump system 50 connected to suction tubing 52 for providing suction to a cannula 54 having a stop cock 55. In some embodiments, the pump system 50 includes a peristaltic pump. While the cannula 54 is only shown as providing a suction flow path, in some embodiments, the cannula 54 can be used to define a portal into the surgical site into which other types of tools or devices can be placed. Such devices include cutting tools, irrigation devices and other surgical instruments. The pump system 50 communicates with the system controller 34 via the network 40. While a single suction tubing 52 is shown connected to the pump system 50, in some embodiments a plurality of suction tubings from different devices may connect to the pump system.

The surgical control system 30 includes a wall suction unit 56 and suction tubing 57 which connects the suction unit to the cutting tool 42 via the cutting tool handpiece 44 to provide suction for removing debris resulting from tool operation. The wall suction unit 56 includes an adjustment valve (not shown) for controlling the suction for tubing 57. In some embodiments, the valve is automatically adjusted by the controller 34 to automatically vary the pressure within tubing 57. While pump system 50 provides suction for tubing 52, in some embodiments the pump system 50 does not provide suction. Instead, wall suction unit 56 provides suction to tubing 52 and additional tubing. The wall suction unit 56 can have control valves to control suction separately for each tubing connected thereto. In some embodiments, a portable suction unit is provided when a wall suction unit is not available.

The surgical control system 30 also includes a camera control unit (CCU) 60 that communicates via the network 40 with the system controller 34. The camera control unit 60 connects via video signal line 62 to a video camera 64 that is mounted onto or is integral with a video camera/light source handpiece 66 disposed within a cannula 67 providing access to a surgical site as shown in FIG. 2. The handpiece 66 is configured to output light to a surgical site. In some embodiments, a separate connection 68 (shown in broken line in FIG. 2) is provided to transfer the video signal from the camera control unit 60 directly to the system controller 34. In some embodiments, the handpiece 66 includes a C-mount endoscope having a focus ring and a camera head with a video camera that is attached to the proximal end thereof.

A light source controller 70 communicates with the system controller 34 via the network 40 and controls power to a light source 74 that provides light to the handpiece 66 via light source optical fiber 72. In other embodiments, the optical fiber 72 is replaced by a power line that provides power to a light source mounted in the handpiece 66. In some embodiments, the video camera/light source handpiece 66 has a video camera (not shown) provided at the distal end of the handpiece, instead of the video camera 64 located at a proximal end of the handpiece.

Irrigation tubing 76 connects the pump system 50 to the cannula 67 to provide irrigation fluid to the handpiece 66. The fluid is output to irrigate surgical site 80. A stop cock or valve (not shown) controls irrigation fluid into the cannula 67. The irrigation fluid follows a path between the inner wall of the cannula 67 and about the outer periphery of the video camera/light source handpiece 66 to the surgical site 80 at the distal end of the cannula. The video camera/light source handpiece 66 both projects light outwardly at the distal end thereof and senses video images with the video camera 64.

Video display 78 shown in FIG. 2 communicates with the system controller 34 over the network 40. The video display 78 displays the video image taken at a surgical site 80 by the video camera 64. In some embodiments, a video display signal line 82 (shown in dotted lines in FIG. 2) is provided for directly connecting the camera control unit 60 to the video display 78.

In FIG. 2, the handpieces 44, 66 and cannulas 54, 67 are oriented within surgical site 80 for conducting a surgical procedure.

In the surgical control system 30, the system controller 34 receives inputs from the cutting tool controller 46, pump system 50, video camera control unit 60 and the light source controller 70. The video display 78 typically is a high definition LCD display whereat the image taken by the video camera 64 of the handpiece 66 is displayed continuously.

The input device 38 of the system controller 34 in some embodiments is a touch screen, while in other embodiments the input device is a set of contact switches or the like. Further, the input device 38 may include a voice recognition system for processing voice commands to provide control signals to the system controller 34.

In one embodiment, video signals from the camera control unit 60 are, instead of being provided over the network 40, simply sent separately and wirelessly to the system controller 34 and to the video display 78.

While pump system 50 is shown in FIG. 2 as having one suction input and one irrigation output, it is contemplated that the pump system may have a plurality of suction inputs. Wall suction unit 56 with valve control can connect to the suction tubing 52 as well as other tubing, so that the pump system 50 only comprises an irrigation pump. A portable pump system for providing irrigation is also contemplated.

Video Signature Identification and Image Control Routine

Figure 3:
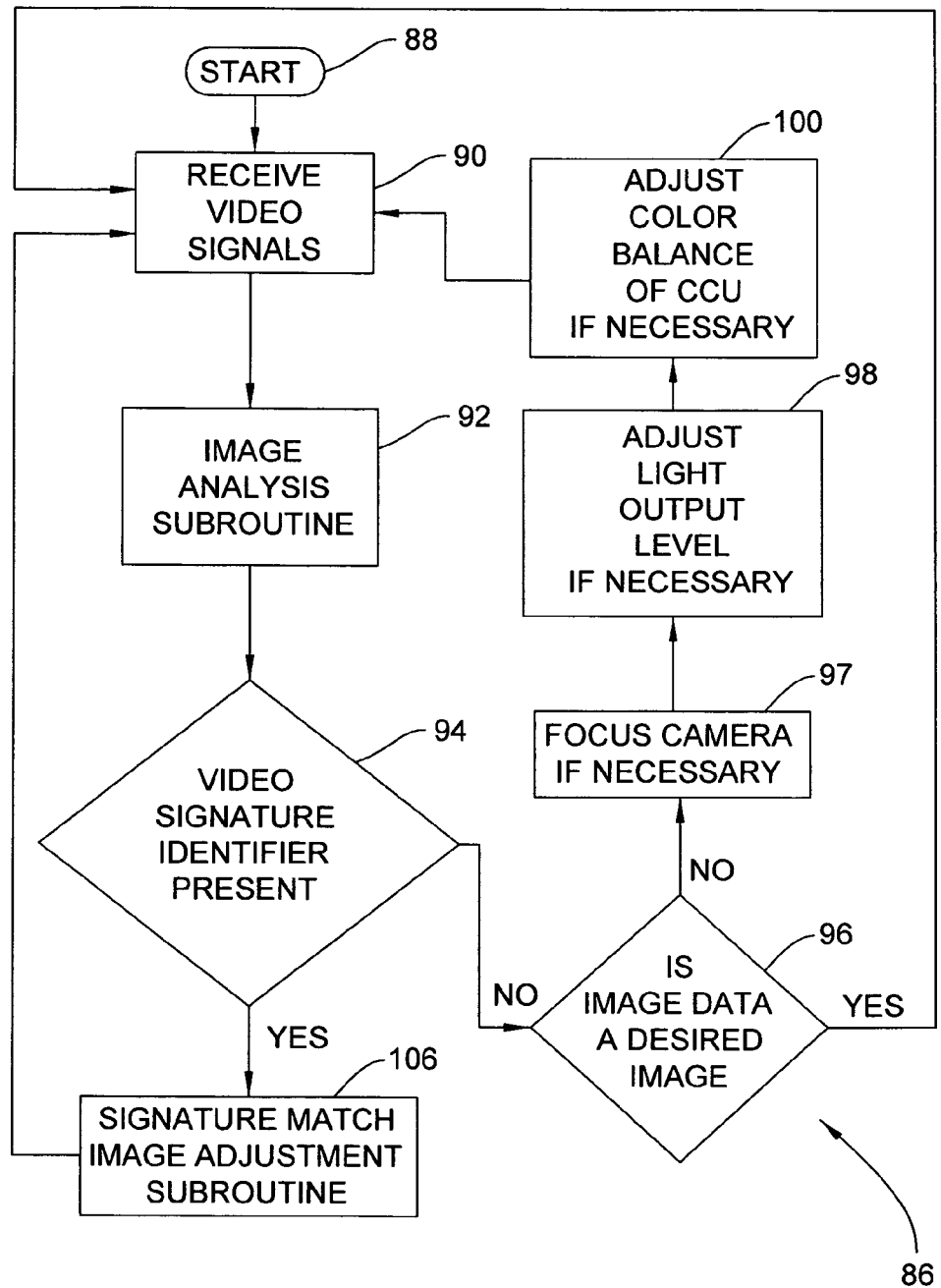
FIG. 3 is a flow chart showing steps for a video signature identification and image control routine that operates to provide an enhanced image of a surgical site.

FIG. 3 is a flow chart representing a video signature identification and image control routine 86 for the system controller 34 that controls the devices of the surgical control system 30. The video signature identification and image control routine 86 begins at start 88. From start 88, the video signature identification and image control routine 86 advances to signal receiving step 90 wherein the system controller 34 receives video signals from the camera control unit 60 and advances to image analysis subroutine 92. In other embodiments, the camera control unit 60 performs the image analysis. In some embodiments, the camera control unit 60 is mounted with the camera 64 that is located at the proximal end of the video camera/light source handpiece 66.

At image analysis subroutine 92, the system controller 34 analyzes image data taken from the video signals for determining the presence of video signatures and stores identifiers in response to matches as shown in the flow chart of FIG. 4 discussed in detail later herein.

Returning to FIG. 3, the image control routine 86 then advances from image analysis subroutine 92 to video signature match step 94. At decision step 94, system controller 34 looks for the presence of stored identifiers corresponding to the various video signatures as determined by and stored in the controller during operation of the image analysis subroutine 92.

In instances where the image analysis subroutine 92 does not find a video signature that matches with a predetermined stored video signature, no identifier is present at decision step 94, and the identification and image control routine 86 advances to image data decision step 96.

At decision step 96, at least a portion of the image data previously analyzed at subroutine 92 is compared with optimal desired image data properties. If the analyzed image is considered appropriate, the routine 86 advances from step 96 by returning to step 90 to receive new video signals. The routine 86 is then repeated.

At step 96, when the video image is not at a maximized quality level, the system controller 34 advances to camera focus step 97. At step 97, focus of a lens (not shown) or the like provided with the video camera/light source handpiece 66 is automatically controlled to maximize the clarity of the video images. The system controller 34 then advances to light adjustment step 98. At step 98, the output level of the light source 74 is either increased or decreased depending on the amount of light necessary to maximize the quality of the video image taken by video camera 64 for display on the video display 78. After light adjustment step 98, the image control routine 86 advances to color balance adjustment step 100.

At color balance adjustment step 100, the system controller 34 adjusts, if necessary, the color balance of the camera control unit 60 for the video images provided by the video camera 64. After color balance adjustment step 100, the image control routine 86 advances to video signal receiving step 90 and repeats the video signature identification and image control routine 86.

In some embodiments, the color balance is adjusted internally by the camera control unit 60 before a signal is output by the camera control unit 60. In other embodiments, the system controller 34 performs calculations and provides an output to control the camera control unit 60.

The order of adjustment steps 97, 98, 100 as shown in FIG. 3 is for purposes of illustration only. The steps 97, 98, 100 may be performed in any order or performed essentially simultaneously by the system controller 34.

Returning to video signature identifier present step 94, in an instance wherein a video signature identifier is stored in the controller 34, the controller advances the routine 86 to the signature match adjustment subroutine 106 as shown in the flow chart of FIG. 6 and discussed later herein. Upon adjustment of the video image at subroutine 106, the controller 34 returns to step 90 of the video signature identification and image control routine 86 as shown in FIG. 3, to receive new video signals and to repeat execution of the video signature identification and image control routine 86.

Image Analysis Subroutine

The image analysis subroutine 92 shown in FIG. 4 operates as follows. The subroutine 92 begins at start 148 and advances to process video image signals step 150 to obtain video signature information from received video images. At step 150, the system controller 34 may conduct a plurality of subcalculations or signature identification type operations on a video image, including comparisons with a sequence of previously stored video images.

Image analysis subroutine 92 then advances to identify fast dispersion areas step 152. At step 152, processed video signals are compared with previously received and stored processed video signals to identify the presence of video signatures for fast dispersion red areas (bleeders) within subsequent video images whereat blood is spreading at at least a predetermined minimum rate. If a bleeder is occurring, the subroutine 92 advances to store identifier (ID) step 154. At step 154, the system controller 34 then stores an identifier or identification code identifying the presence of a bleeder in the video images for later control purposes.

The controller 34 then advances the subroutine 92 to find black/white (B/W) transitions decision step 156. If an identification of a video signature for fast dispersion red areas is not matched at step 152, the image analysis subroutine 92 advances directly to decision step 156.

At black/white transitions decision step 156, processed video signals are compared with a sequence of previously processed video signals to determine, over time, the presence of a video signature match for fast upwardly moving black/white transition, which correspond to upward movement of air bubbles within a liquid. The air bubbles can be generated by operation of an RF cutting tool. If there is a signature match, or in some instances close to a complete signature match, the subroutine 92 advances to storing identifier step 158.

At step 158, the controller 34 stores an identifier indicating the presence of air bubbles in the video image. The controller 34 then advances the subroutine 92 to find objects at multiple distances step 160. If there is not a signature match at step 156, the subroutine 92 immediately advances to find objects at multiple distances step 160.

At find objects at multiple distances step 160, video images are compared to determine the presence of video signatures for multiple small objects at different focal distances within a video image. This signature matching determines the presence of particulates in the fluid at the viewed surgical site 80. If the processed video images result in a video signature or signatures that match a stored video signature or signatures for the presence of particulates, the video image analysis subroutine 92 advances to storing identifier (ID) step 162. The particulates can be debris generated by a burr or other cutting tool.

At storing identifier step 162, a particulate identifier or identifier code is stored in the system controller 34. The subroutine 92 then advances to identify light dispersion step 164.

If there is not a video signature match for the identification of particulates at decision step 160, the subroutine 92 immediately advances to identify light dispersion step 164.

At tissue blocking camera step 168, the controller 34 analyzes the processed video image signal to determine the presence of tissue or like material blocking the distal tip of the video camera/light source handpiece 66 by comparing processed video images with a video signature for the presence of tissue blocking the distal end of the handpiece 66.

If a processed video image has a signature that matches with a stored video signature corresponding to the presence of tissue blocking the camera view, the controller 34 advances the subroutine 92 to store identifier (ID) step 170.

At step 170, a camera tip blocked identifier is stored in the system controller 34 and the subroutine 92 advances to return step 174. If a blocked distal tip for the camera/light source handpiece 66 is not detected at step 168, the controller 34 immediately advances the image analysis subroutine 92 to return step 174.

Figure 4:
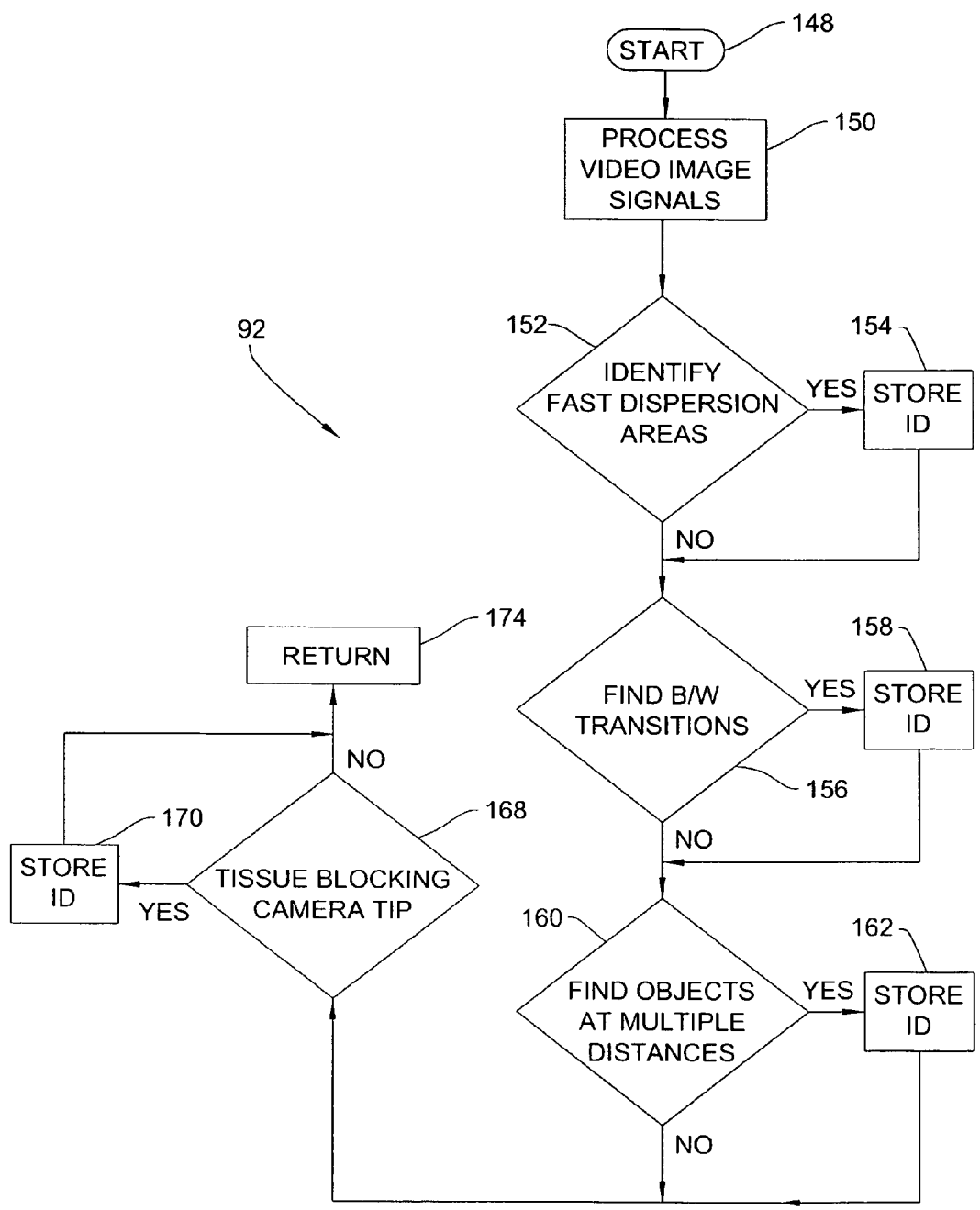
FIG. 4 is a flow chart of a video image analysis subroutine for analyzing video images from a surgical site.

The order of identification steps 152, 156, 160, 168 as shown in FIG. 4, is for purposes of illustration only. The steps 152, 156, 160, 168 in subroutine 92 can be performed in any order, or executed essentially simultaneously.

Upon completion of the identification of the various conditions that can degrade a video image taken at a surgical site 80, the controller 34 advances from return step 174 of the video image analysis subroutine 92 to the video signature identifier present step 94 of the video signature identification and image control routine 86 shown in FIG. 3.

With respect to video image signal processing or video image stream analysis for the image analysis subroutine 92 discussed above, information can be extracted specifically by using color imaging processing algorithms. For instance, bleeders can be determined by using a color image processing algorithm coupled with 2-D spatial information from the sensed video image. For example, close pixels that look like blood can be detected in the video RGB color space by using a simple distance formula. The closer that the pixel distance is to the desired pixel point in the color space, the more likely that the pixel belongs to a digital representation of a bleeder.

While determining and adjusting light output level and color balance is separate from the image analysis subroutine 92 shown in FIG. 3, in some embodiments one or both of the light output level and the color balance of the camera control unit 60 are provided with decision blocks as shown in FIG. 4 and compared with various video signatures in the image analysis subroutine 92.

In some embodiments, swelling/distention of joints can reduce quality of a video image. This situation can be determined by video image analysis and pressure/fluid flow may be controlled to minimize the condition and any negative effect on the video image.

In image analysis subroutine 92, color image processing may also be coupled with other information and techniques, such as fast fourier transform (FFT) spatial frequency information, image segmentation and weighting techniques to weight the different processing quantitative indicators to make automated decisions about the existence of obstructions, such as bleeders, along with particulates and bubbles.

Figure 5:
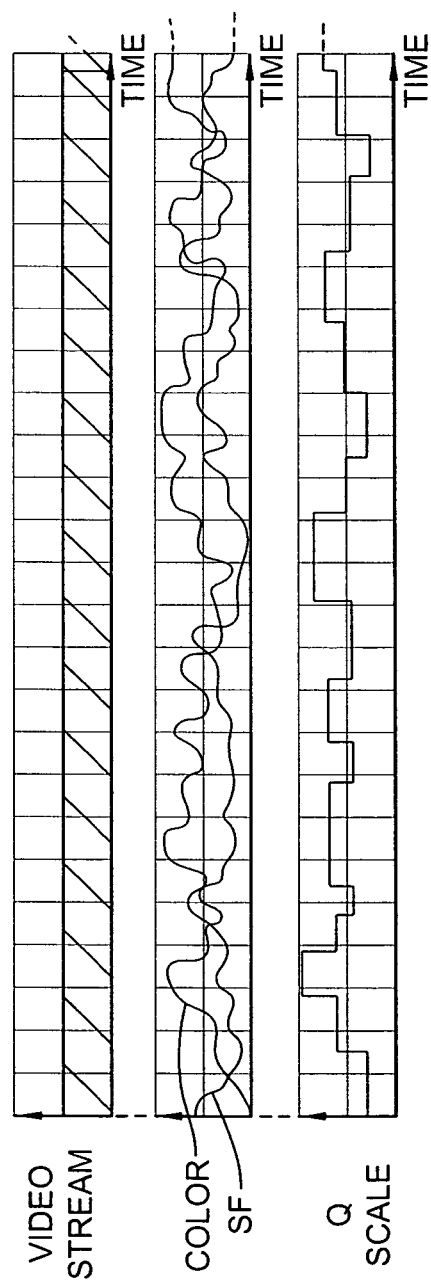
FIG. 5 is a graph of a video signal stream, color signals, spatial frequency and a Q scale.

FIG. 5 illustrates an embodiment wherein a video stream that represents a plurality of sequential video images is analyzed to determine the presence of video signatures. In FIG. 5, color (RED color) and spatial frequency (SF) are determined and shown over time for a stream of video signals. A subjective image quality evaluation provides scaled scores as shown over time on a Q scale as illustrated in FIG. 5. The Q scale values can be used to determine the presence of a video signature or other anomaly. Low spatial frequency values may indicate the presence of blood and high spatial frequencies may indicate the presence of debris. The presence of bubbles may have a unique signature spatial frequency. In response to a video signature match or the like, the controller 34 then stores a predetermined identifier as discussed above.

Additional image analysis techniques are disclosed in U.S. Patent Pub. 2008/0243054, the disclosure of which is hereby incorporated by reference. The '054 patent publication discloses an arthroscopic video camera and video signal processor.

Signature Match Image Adjustment Subroutine

If, at the video signature identifier present decision step 94 in FIG. 3, the controller 34 finds at least one stored identifier present, the controller advances to signature match adjustment subroutine 106. Detailed operation of the signature match image adjustment subroutine 106 is illustrated in FIG. 6.

Figure 6:
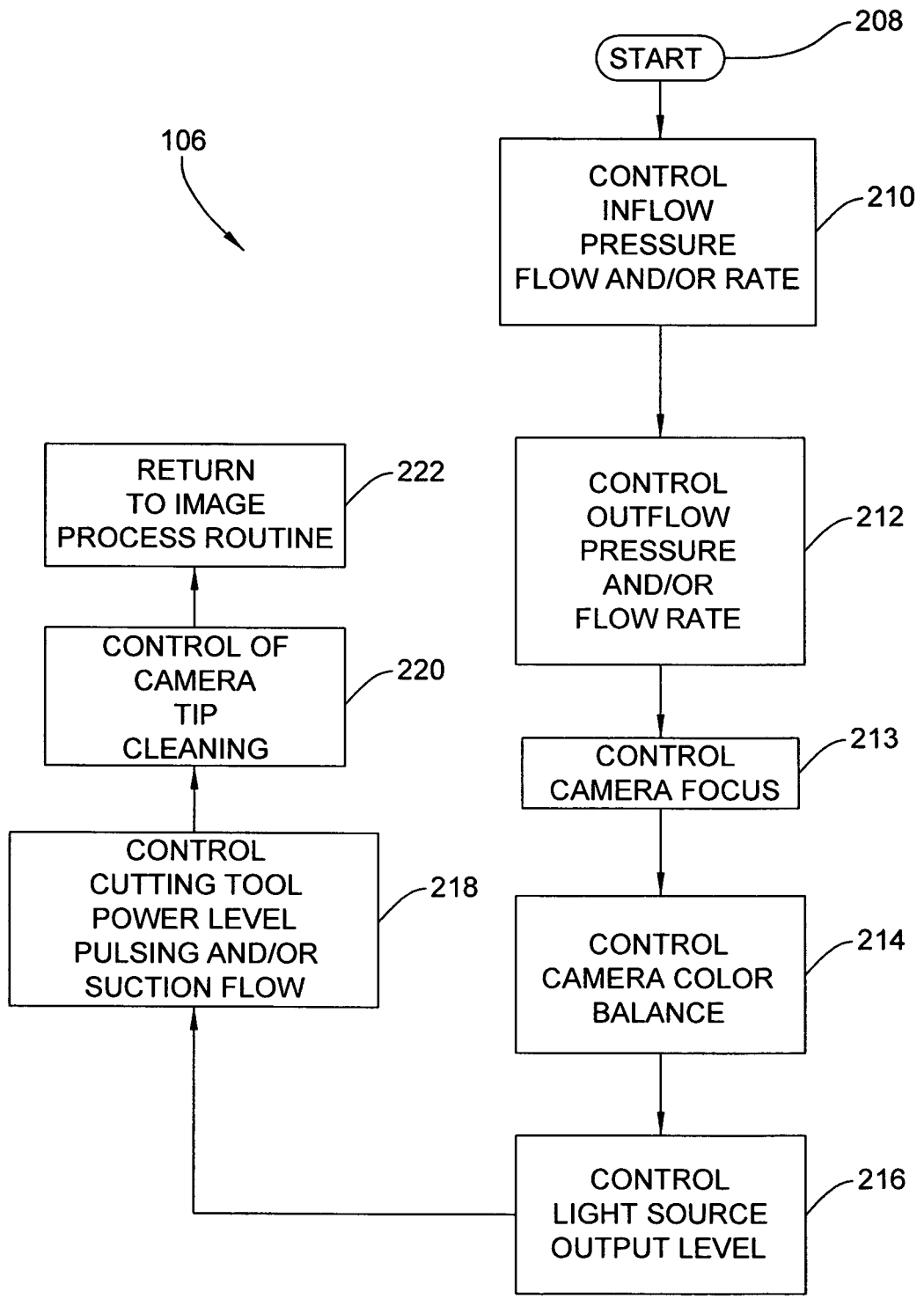
FIG. 6 is a signature match image adjustment subroutine for controlling devices to improve the video image.

From start 208 in FIG. 6, the controller 34 advances the subroutine 106 to control inflow pressure flow and/or flow rate control step 210.

At control step 210, the system controller 34 obtains information on the inflow pressure from a sensor (not shown) associated with the irrigation tubing 76 from the pump system 50 or from a sensor disposed in the handpiece 66. Further, in some embodiments the system controller 34 is provided with gas or liquid pressure sensed within the surgical site 80, as well as the flow rate through return suction tubing 52, 57 and the pressure values thereat. Depending on the measured pressure/flow conditions, and especially the type of condition at the surgical site 80 determined by the matched video signature(s) and provided by the stored identifiers, the controller 34 adjusts inflow pressure and/or flow rate provided to the surgical site at step 210 to improve the quality of the video image taken by video camera 64. The controller 34 then advances the signature match image adjustment subroutine 106 to control outflow pressure and/or flow rate step 212.

At step 212, depending on the video signatures matched, the system controller 34 selectively controls the outflow pressure and/or flow rate through the suction tubing 52, 57. The outflow pressure/flow rate control is dependent in part on the input pressure/flow rate values, and the type of identifiers. For example, in the case of a quantity of increasing blood areas detected by a video signature and provided with an identifier at step 154 as shown in FIG. 4, the inflow/outflow and pressure values can be operated in a manner to flush blood from the surgical site 80 in a timely and effective manner. In some embodiments, pulsing of irrigation fluid entering a surgical site 80 removes the blood and provides a quality video image. The position of the stop cock 55 of the cannula 54 or the valve of wall suction unit 56 can automatically be adjusted by controller 34 to maximize the video image.

While steps 210, 212 are illustrated as separate steps in FIG. 6 for convenience, in some embodiments the steps 210, 212 represent a single step as inflow/outflow control of fluid acts as a single response to correct a sensed undesired condition or plurality of undesired conditions identified by a comparison with one or more video signatures from subroutine 92. The controller 34 then advances the subroutine 106 to camera color balance step 214.

Depending on the properties of the one or more video signature(s) that are determined, selective control of lens focus for the video camera is provided at camera focus step 213. In some instances, the system controller 34 takes no action at step 213 and advances to step 214.

Depending on the properties of the one or more video signature(s) that are matched or determined, selective control of camera color balance occurs in some embodiments at camera color balance step 214. In some instances, especially depending on the type of video signature identifier obtained by the system controller 34, the controller takes no action at step 214 and advances to light source output control level step 216.

At light output control level step 216, the controller 34 signals the light source controller 70 for operating the light source 74 to output more or less light, as necessary, to maximize the video image output by the camera control unit 60. More specifically, the system controller 34 calculates the need for changes or adjustments in the light output level, and then the controller 34 provides signals to the light source controller 70 to carry out the light output level changes. In some instances, the light output level does not change as video image quality with respect to the light level is already maximized.

In some embodiments, the image adjustment subroutine 106 then advances to step 218. Depending on the video signature identifiers that have been determined and stored, the controller 34 may automatically control, for example, operation of the cutting tool 42 (on/off state or rotational/reciprocating speed) and also may control the inflow pressure/flow rate and/or outflow pressure/flow rate essentially simultaneously to unclog the cutting tool 42, or to otherwise improve the video image taken of the surgical site 80 by camera 64. In some embodiments, a pulsing pressure and/or liquid flow is also applied to clean or unplug material at or near a cutting tool. In some embodiments, if bubbles are detected by image analysis, an RF cutting tool that presumably is generating the bubbles is controlled by the controller 34 to operate in a different power mode or powered off to minimize the formation of bubbles.

In instances where the cutting tool 42 is not in operation, or no identifier requires an action thereby, control of the cutting tool does not occur, and the image adjustment subroutine 104 simply advances the subroutine 106 to control of camera tip cleaning step 220. In some embodiments, cutting tool control step 218 is not provided in the image adjustment subroutine 106.

At step 220, if the controller 34 stores a camera cleaning identifier that corresponds to a video signature caused by material or tissue disposed at the distal end of the video camera/light source handpiece 66 shown in FIG. 2, then the controller 34 controls an apparatus known in the art to clean the distal tip of the handpiece 66 to obtain a desired improved image.

In some embodiments, the inflow of irrigation liquid is redirected by a structure adjacent or near the distal end of the handpiece to remove the tissue. In other embodiments, when a tip cleaning identifier is provided, the other control steps, such as camera color balance and light output level control are by-passed. The controller 34 advances the image adjustment subroutine 106 directly to tip cleaning step 220 and then to return step 222.

At return step 222, the system controller 34 returns to the video signature identification routine 86 shown in FIG. 3 to receive video signals at step 90 and repeat execution of the routine 86 to again determine the presence of video signature matches.

In some embodiments, the operating status of output devices or tools are either monitored by or input to the system controller 34. In response to the status of the devices or tools, the controller 34 can control pressure and/or suction values, as well as control tool operation, to maintain a quality image free from video signatures. For example, in some embodiments the system controller 34 provides output signals to drive the various cutting devices or receives input signals when a tool is manually operated. Thus, the system controller 34 is capable of controlling inflow pressure flow and/or flow rate, as well as outflow suction and/or flow rate, depending on the tools being operated. This arrangement enables the system controller 34 to initially prevent the degradation of picture quality and thus avoid requiring a later action in response to a video signature to improve the picture quality.

For example, when a burr or other cutting device is operating, the system controller 34 can immediately control suction and/or irrigation to remove debris before video image quality is degraded.

Laparoscopic System

Figure 7:
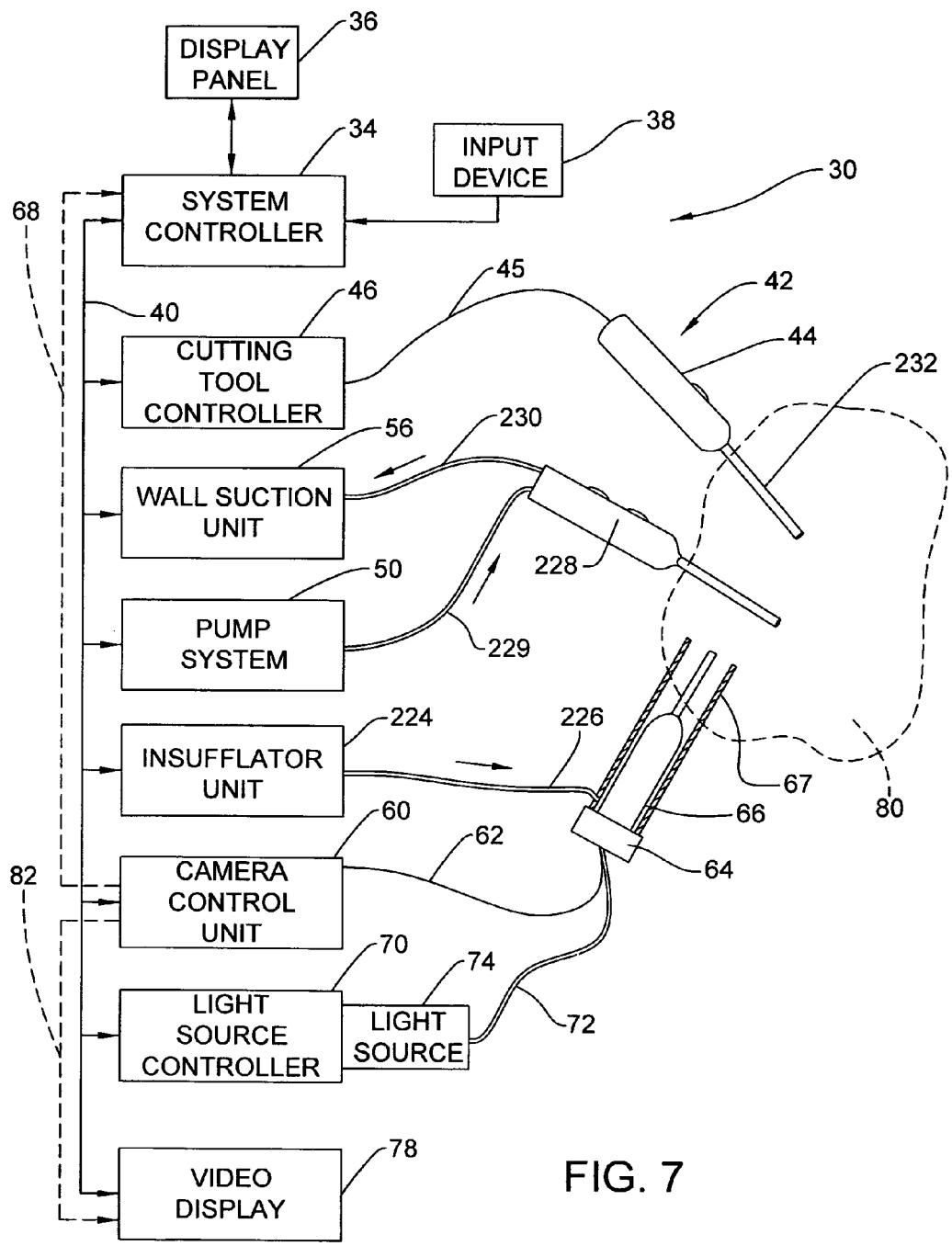
FIG. 7 depicts a block diagram of a laparoscopic integrated surgical control system, along with surgical tools disposed at a surgical site.

The surgical control system 30 illustrated in FIG. 7 generally corresponds to the system illustrated in FIG. 2 (like numbers utilized for the same parts), except the system is a laparoscopic surgical system.

The surgical system 30 includes an insufflator unit 224 having air supply tubing 226 for supplying air, preferably carbon dioxide, to a trocar 267 that receives the video camera/light source handpiece 66. Thus rather than supplying irrigation to surgical site 80, the trocar 267 receives fluid, such as air or $CO_2$, between an inner wall of the trocar and the periphery of the handpiece 66 that flows outwardly from the distal end of the trocar to expand a peritoneal cavity to enable access to a surgical site 80.

The pump system 50 and wall suction unit 56 shown in FIG. 7 connect to a suction/irrigation tool 228. The pump system 50 provides fluid to the tool 228 via irrigation tubing 229. The wall suction unit 56 provides suction to the suction/irrigation tool 228 via suction tubing 230. The suction/irrigation tool 228 selectively irrigates and suctions the surgical site 80. In some embodiments, the wall suction unit 56 is replaced by a portable suction unit.

The cutting tool 42 shown in FIG. 7 includes the handpiece 44 receiving an electrode 232. In some embodiments, the cutting tool 42 typically is an electrocautery device with the electrode 232 being capable of cutting tissue and a coagulation function.

In some embodiments, the video camera/light source handpiece 66 comprises an endoscope having an eyepiece that is joined at a proximal end to a camera head having a coupler.

The arrangement shown in FIG. 7 operates in a similar manner to the arrangement shown in FIG. 2. The suction/irrigation tool 228 typically is only manually controlled for irrigating surgical site 80 and for withdrawing irrigation fluid as necessary.

The system controller 34 and network 40 communicate with and operate the various devices in essentially the same manner as shown in FIG. 3 and discussed above.

Figure 8:
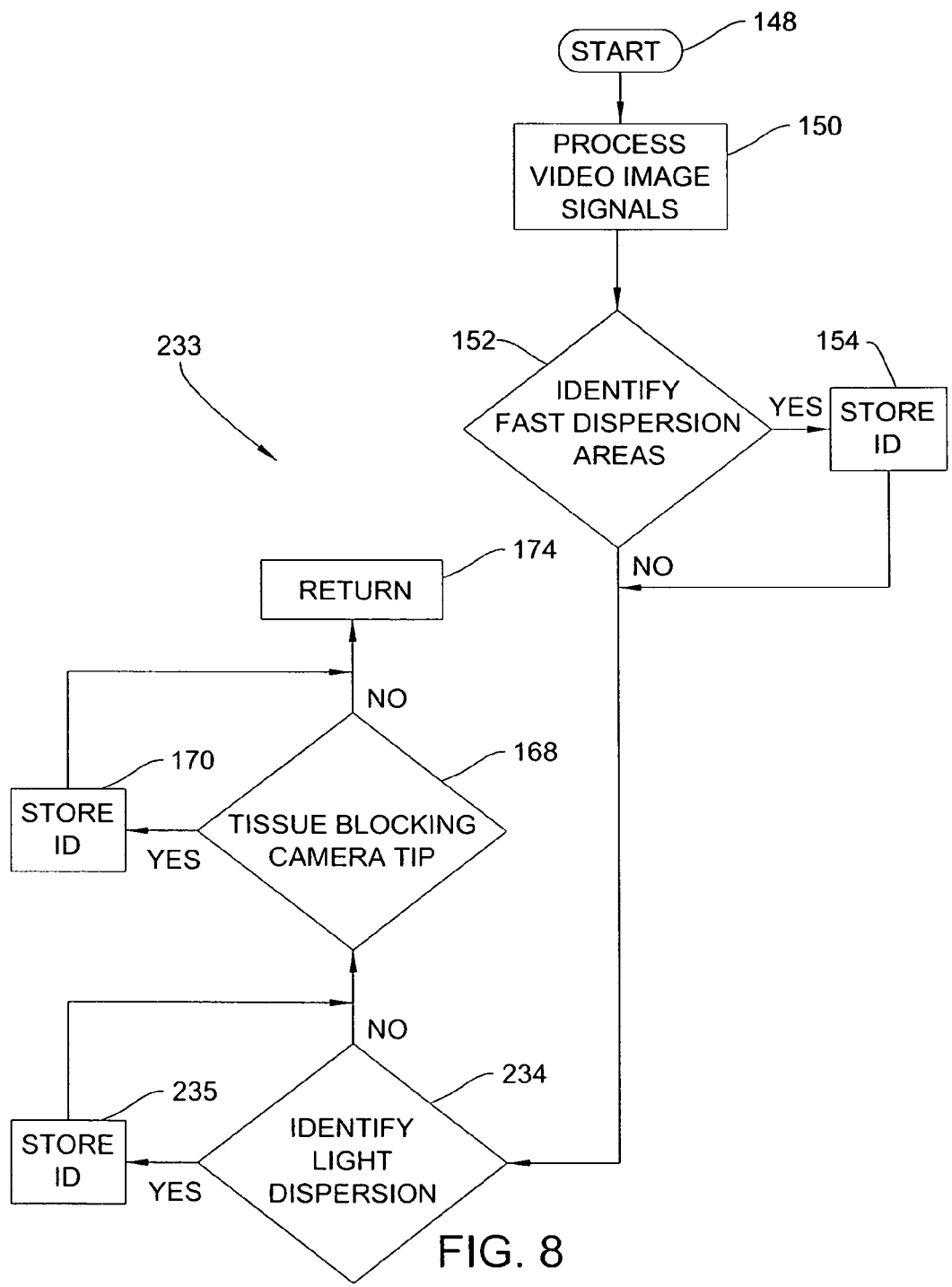
FIG. 8 is a flow chart of a video image analysis subroutine for analyzing video images from a surgical site.

FIG. 8 shows a video image analysis subroutine 233 similar to the arrangement described above with respect to FIG. 4 (same numbers perform the same function).

In the video image analysis subroutine 233, steps 150, 152, 154 function in the same manner as set forth above. After comparing video signatures for fast dispersion areas (bleeders) at step 152, and if found, storing a bleeder identifier at step 154, the controller 34 advances the video image analysis subroutine 233 to light dispersion identification step 234.

At light dispersion identification step 234, the system controller 34 operates to compare a sequence of processed video signals with predetermined and stored light dispersion video signatures to determine the presence of smoke. If there is a signature match between the processed video signal and a stored video signature for the presence of smoke, the controller 34 advances the subroutine 92 to store identifier (ID) step 235.

At store identifier step 235, a smoke presence identifier is stored in the system controller 34. Then, the controller 34 advances the subroutine 233 to tissue blocking camera tip decision step 168.

If a video signature for the presence of smoke is not identified by the controller 34 at step 235, the controller 34 immediately advances the subroutine 233 to decision step 168.

At tissue blocking camera tip decision step 168, besides the possibility of tissue on the lens of the camera/light source handpiece 66, the presence of blood or the like on a lens and thus blocking the image for the video camera 64 can be determined as a video signature match. If a match is formed, the controller 34 advances to store identifier (ID) step 170 and thus stores an identifier.

After store identifier step 170, the controller 34 advances to return 174 and returns to the video signature identification and image control routine 86 shown in FIG. 3. If there is no detection of tissue blocking of the camera 64 at decision step 168, the controller 34 immediately advances to return step 174 and returns to routine 86.

The order of steps 152, 234, 168 in subroutine 233 is provided for purposes of illustration only. The steps can be performed in any order, or essentially simultaneously.

In the laparoscopic surgical system, the signature match adjustment subroutine therefore is similar to the signature match adjustment subroutine 106 shown in FIG. 6. A main difference is that the control of pressure steps 210, 212 are limited. In the laparoscopic surgical system, in the event that smoke is detected by the video images from the surgical site, the suction/irrigation tool 228 can automatically operate to remove smoke with the wall suction unit 56 via tubing 230. At the same time, the insufflator unit 224 provides additional gas via the handpiece 66 to the surgical site 80 for preventing the peritoneal cavity from collapsing. Further, power to the electrode 232 of an electrocautery device can be reduced or interrupted, if necessary, to limit the production of additional smoke.

With respect to both arthroscopic and laparoscopic surgical systems, the cause of bleeding is less certain than other conditions resulting in degraded image quality. Therefore, in some embodiments, when a bleeder is detected and none of the tool devices are operating, the system controller 34 determines the tool device or devices that were most recently operated. The system controller 34 can utilize this information to assist in determining what operations of fluid input/output, fluid pressure, or even which of plural fluid input/output devices to select for removing the bleeder from the video image.

Multi-Band Light Source Control Image Analysis Subroutine

Figure 9:
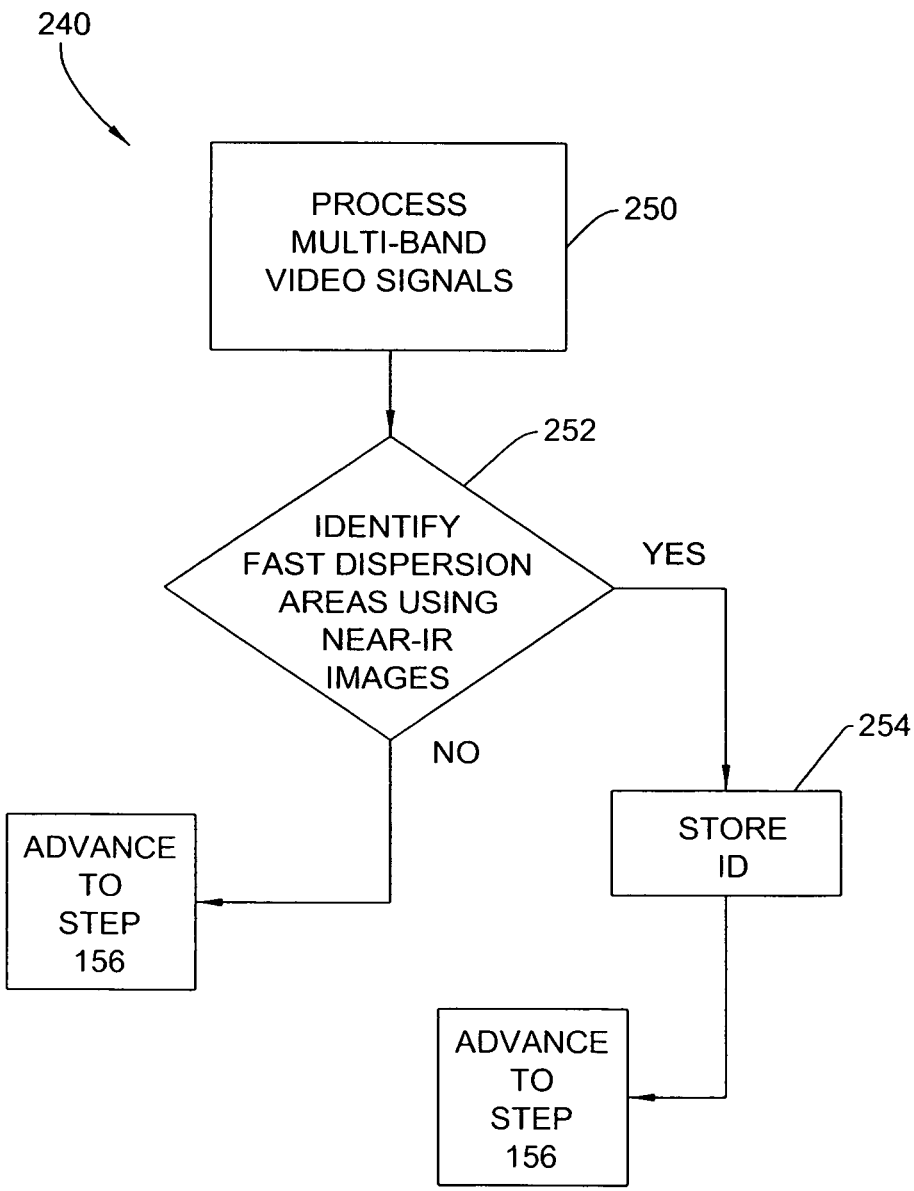
FIG. 9 is a flow chart for a multi-band light source control image analysis subroutine.

Multi-band light source control image analysis subroutine 240 shown in FIG. 9 includes steps 250, 252, 254. The steps 250, 252, 254 are a substitute for steps 150, 152, 154 in the video image analysis subroutine 92 shown in FIG. 4 and discussed above.

In multi-band light source control image analysis subroutine 240, the light source controller 70 additionally controls the light source 74 to periodically strobe or pulse the light source 74 to output additional non-visible near-infrared (IR) light at predetermined intervals. Since the additional near-infrared light is outside of the visible spectrum, the additional light is not viewable by a surgeon. Further, one or more bands or wavelengths of non-visible light can be provided at short time intervals, such as milliseconds. Finally, in some embodiments, various wavelengths of non-visible light are output simultaneously.

Since hemoglobin absorbs light in the 800 nm-1,000 nm (near-infrared) range, blood is visible as distinct dark points when reflected near-IR light images are received by video camera 64. The dark points provide more detailed information for an image processing algorithm to determine the presence of blood in an image, as compared to analyzing colors. Thus, instead of identification of fast dispersion areas at step 152 in FIG. 4 as discussed above, pulsed or strobed near-infrared signals, not viewable by the surgeon, are included with visible light and utilized to better determine the presence of fast dispersion red areas corresponding to bleeders within the video image obtained by the video camera 64.

To execute the multi-band light source control image analysis subroutine 240 shown in FIG. 9, the light source 74 is controlled by light source controller 70 to provide multi-band light source outputs to illuminate a surgical site 80, including providing near-infrared or other non-visible light at predetermined intervals. At processing multi-band video signals step 256 shown in FIG. 7, the controller 34 processes video image signals that include the periodic reflected IR signals received by the video camera 64. Thus, step 250 essentially corresponds to step 150 shown in FIG. 4, except the additional periodic IR signals are also processed.

The light source control image analysis subroutine 240 then is advanced by the controller 34 to step 252 shown in FIG. 9. At step 252, the controller 34 identifies the presence of bleeders in view of the IR signals sensed by the video camera 64 in comparison with corresponding non-visible video signatures for a video signal. Thus, step 252 corresponds in part to step 152 shown in FIG. 4, except IR signals are processed instead of, or in addition to, visible color signals.

If a dispersion area is found at identify fast dispersion areas decision step 252, the controller 34 advances to stop identifier (ID) step 254. At step 254, the controller 34 stores an identifier corresponding to the presence of bleeders. Thus, step 254 is essentially identical to step 154 shown in FIG. 4.

Regardless of the identification of a bleeder, the light source control image analysis subroutine 240 shown in FIG. 9 advances to step 156 as shown in the subroutine 92 of FIG. 4.

In conclusion, the multiband light source control image analysis subroutine 240 corresponds to and replaces flowchart blocks 150, 152, 154 shown in FIG. 4. The main difference between the flow chart shown in FIG. 9 from the corresponding portion of the flow chart illustrated in FIG. 4, is the use of IR light to determine the presence of dispersion areas, rather than color analysis.

Leak/Clog Detection Subroutine

Figure 10:
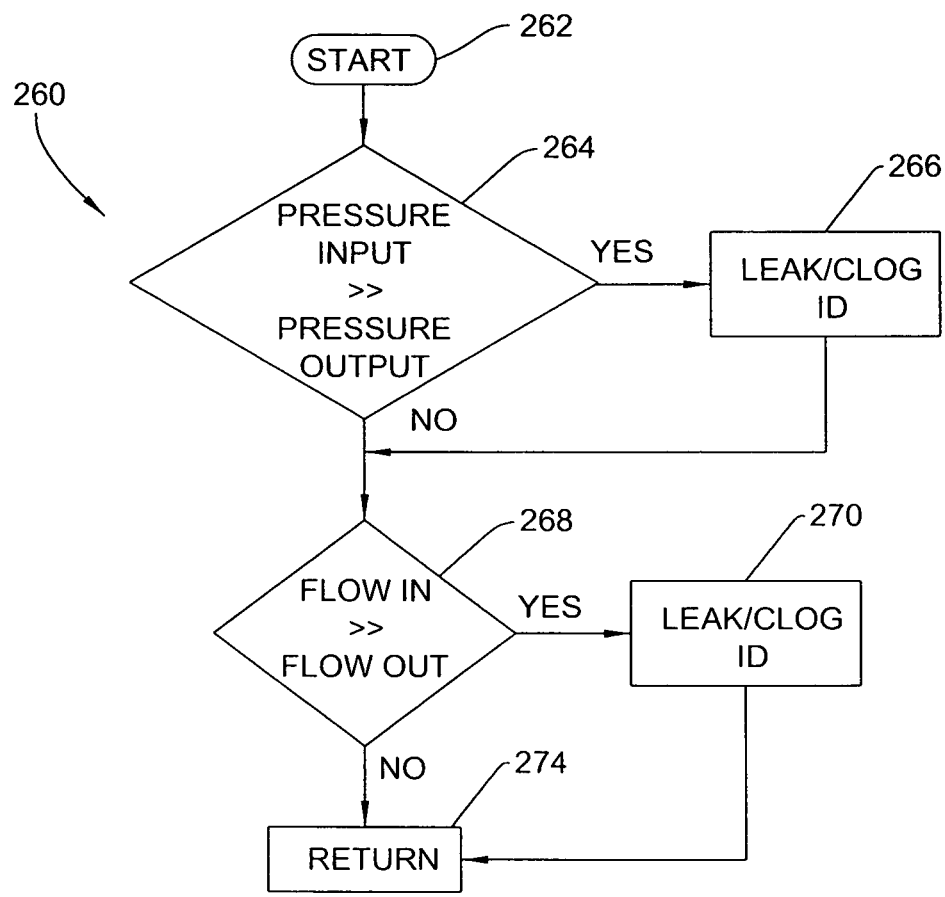
FIG. 10 is a flow chart of a leak/clog subroutine of the invention.

In another embodiment of the invention, a leak/clog detection subroutine 260 shown in FIG. 10 is also provided for use with the routine 86 shown in FIG. 3. The subroutine 260 operates to determine the presence of greater than expected fluid leakage at the operating site 80 or greater than expected fluid pressure in the flow paths.

In FIG. 10, the subroutine 260 begins at start 262 and advances to step 264. At pressure comparison step 264 the input pressure, typically determined from the pump system 50 or from a sensor associated with irrigation tubing 76 is measured and compared with an output pressure (suction) determined by a pressure sensor provided with a suction port of pump system 50 or otherwise pressure sensors disposed in suction flow paths of tubing 52, 57 or within the cutting tool handpiece 44. When the system controller 34 determines that the pressure input and pressure output differ by a predetermined amount, the subroutine 260 advances to leak/clog store identifier (ID) step 266 and stores a clog identifier in the system controller 34. Thereafter, whether or not a clog is identified, the system controller 34 advances the subroutine 260 to decision step 268.

At flow decision step 268, the system controller 34 determines whether the measured fluid flow through the irrigation tubing 76 that enters the cannula 67 between the inner wall thereof and the periphery of the camera/light source handpiece 66 and advances to the distal end of the cannula and enters the peritoneal cavity exceeds the fluid flow through the suction tubing 52, 57 by a significant amount. If the flow difference is significant enough to determine that an issue exists at the surgical site 80, such as significant leakage of fluid into the body of a patient, a leak identifier is stored in the system controller 34 at step 270. Whether or not a leak is discovered at step 268, the routine 260 advances to return step 274 as shown in FIG. 10.

As a result of the sensing of a clog, the fluid input and/or the fluid output can be automatically pulsed or varied by the controller 34. Further, the driving of the cutting tool 42 can be automatically pulsed/stopped by the controller 34 in an attempt to unclog the suction path of the handpiece.

In some embodiments, the leak/clog detection subroutine 260 is operated periodically by the system controller 34 as a part of a routine that is different from the routine 86 illustrated in FIG. 3.

Although a particular preferred embodiment of the invention has been disclosed in detail for illustrative purposes, it will be recognized that variations or modifications of the disclosed apparatus, including the rearrangement of parts, lie within the scope of the present invention.

What is claimed is:

1. A video based image detection/identification system for fluid and visualization control of a laparoscopic surgical system for providing an acceptable video image of a surgical site, comprising:
 a cauterizing tool for manipulating tissue at the surgical site;
 an insufflator for providing gas to the surgical site;
 an adjustable suction system for providing suction at the surgical site for controlling removal of gas from the surgical site;
 a light source for providing light to the surgical site;
 a video sensing device for obtaining video signals of video images at the surgical site;
 an image display for displaying the video images; and
 a system controller configured to maintain quality of the video images obtained by the video sensing device and provided to the image display, wherein the system controller receives and processes the video signals to identify a video signature corresponding to a condition that interferes with a quality of the video images;
 the system controller interacting with the cauterizing tool, the insufflator and the adjustable suction system and controlling at least one of the cauterizing tool, the insufflator and the adjustable suction system to address the condition of the surgical site to return the video images from the video signals to an acceptable quality for viewing so that a user is free from having to manually control any of the cauterizing tool, the insufflator, the adjustable suction system, and the video sensing device to obtain the acceptable video image of the surgical site for viewing on the image display;
 wherein the video signature to be identified comprises smoke, and the system controller operates at least one of the cauterizing tool, the insufflator and the adjustable suction system in response to an amount of smoke sensed.

2. The system according to claim 1, wherein the system controller adjusts a power output of the cauterizing tool between a low power output level and a high power output level.

3. The system according to claim 1, wherein the system controller analyzes the video signals to determine a second video signature corresponding to debris on a tip at a distal end of a housing of the video sensing device, the system controller controlling a tip cleaning device in response to the sensing of debris at the tip of the housing.

4. The system according to claim 1, wherein the system controller uses color image processing comprising a FFT spatial frequency information technique to process the video signals.

5. A method for controlling a surgical system to provide an acceptable image of a surgical site for display during laparoscopic surgery, comprising:
 manipulating tissue at the surgical site with a cauterizing tool;
 providing gas to the surgical site from an insufflator;
 suctioning the surgical site with an adjustable suction system to controllably remove gas from the surgical site;
 providing light energy to the surgical site so that the surgical site is viewable;
 obtaining video image signals at the surgical site with a video sensing device for use in displaying video images on a video display;
 analyzing the video image signals to determine the presence of smoke that reduces visibility or clarity of the video image signals;
 configuring a system controller to control the cauterizing tool, the insufflator and the adjustable suction system;
 in response to sensing a lack of quality and clarity of the video images because of the smoke, controlling at least one of the cauterizing tool, the insufflator and the adjustable suction system with the system controller to provide an acceptable video image quality for viewing without any manual control or manual input from a tool operator; and
 displaying the video images on the video display.

6. The method according to claim 5, wherein the step of analyzing the video image signals includes comparing portions of the video image signals to stored video signatures corresponding to conditions that interfere with the quality of the video image signals.

7. A video based image detection/identification system for fluid and visualization control of an arthroscopic surgical system for providing an acceptable video image of a surgical site, comprising:
 a cutting tool for manipulating tissue at the surgical site;
 a liquid pump system for providing fluid to the surgical site;
 a first adjustable suction system providing suction from the cutting tool through first suction tubing for controlling removal of fluid from the surgical site;
 a second adjustable suction system providing suction at the surgical site through second suction tubing also for controlling removal of fluid from the surgical site;
 a light source for providing light to the surgical site;
 a video sensing device for obtaining video signals of video images at the surgical site;
 an image display for displaying the video images; and
 a system controller maintaining quality of video images obtained by the video sensing device and provided to the image display, wherein the system controller receives and processes the video signals to determine a video signature corresponding to a condition that interferes with the quality of the video images, wherein the system controller independently controls a first suction of the first adjustable suction system, a second suction of the second adjustable suction system and an output of the cutting tool between a low cutting level and a high cutting level to address a condition of the fluid at the surgical site to return the video images from the video signals to an acceptable quality for viewing so that a user is free from having to manually control any of the cutting tool, the liquid pump system, the light source, and the video sensing device to obtain the acceptable video image of the surgical site for viewing on the image display.

8. The system according to claim 7, wherein the video signature to be determined corresponds to at least one of bubbles, debris, particles, and bleeders.

9. The system according to claim 8, wherein the cutting tool comprises an RE cutting tool, and wherein the system controller controls the RF cutting tool in response to bubbles identified from the video signals by the system controller to return the video images of the video signals to the acceptable quality for viewing.

10. The system according to claim 9, wherein the system controller analyzes the video signals to determine a video signature corresponding to debris on a tip at a distal end of a housing of the video sensing device, the system controller controlling a tip cleaning device in response to the sensing of debris at the tip of the housing.

11. The system according to claim 7, wherein the system controller controls the light source to adjust an output of predetermined wavelengths of energy to different predetermined output levels for sensing preselected conditions.

12. The system according to claim 11, wherein the predetermined wavelengths of energy are output intermittently.

13. The system according to claim 11, wherein the predetermined wavelengths of energy include near infrared energy for at least assisting in determining the presence of a bleeder or of blood in the video images of the video signals.

14. The system according to claim 7, wherein the system controller uses color image processing comprising a FFT spatial frequency information technique to process the video signals.

15. The system according to claim 7, wherein the cutting tool is a mechanical cutting tool.

16. A method for controlling an arthroscopic surgical system to provide an acceptable image of a surgical site for display, comprising:
 manipulating tissue at the surgical site with a cutting tool;
 outputting fluid to the surgical site from a liquid pump system;
 providing a first adjustable suction system providing suction from the cutting tool through first suction tubing for controlling removal of fluid from the surgical site;
 providing a second adjustable suction system providing suction at the surgical site through second suction tubing also for controlling removal of fluid from the surgical site;
 providing light energy to the surgical site so that the surgical site is viewable;
 obtaining video image signals at the surgical site with a video sensing device for use in displaying video images on a video display;
 analyzing the video image signals to determine presence of factors that reduce visibility or clarity of the video image signals;
 in response to sensing a lack of quality and clarity of the video images, independently controlling a first suction of the first adjustable suction system, a second suction of the second adjustable suction system and a cutting level of the cutting tool between a low cutting level and a high cutting level so that the video images detected by the video image signals is controlled to provide an acceptable image quality for viewing without any manual control or manual input from a cutting tool operator; and
 displaying the video images on the video display.

17. The method according to claim 16, wherein a camera/light source handpiece includes a camera and a light source, the camera/light source handpiece being disposed within a cannula that provides access to the surgical site, and further comprising controlling a flow of irrigation fluid between an outer periphery of the camera/light source handpiece and an inner wall of the cannula, wherein the fluid enters the surgical site via a distal end of the cannula.

18. The method according to claim 16, wherein the step of analyzing the video image signals includes comparing portions of the video image signals to stored video signatures corresponding to conditions that interfere with the quality of the video image signals.

19. The method according to claim 18, wherein the surgical system comprises an endoscopic system, and the video signatures are provided for bubbles, debris, particles and bleeders.

20. The method according to claim 16, including providing the light energy to the surgical site so that the surgical site is viewable for the video sensing device and providing non-visible light at one or more predetermined wavelengths for assisting the analyzing step in determining the presence of bleeders within the video images.

21. The method according to claim 16, wherein the cutting tool is a mechanical cutting tool.

\* \* \* \* \*

UNITED STATES PATENT AND TRADEMARK OFFICE
CERTIFICATE OF CORRECTION

| | |
|---|---|
| PATENT NO. | : 9,066,658 B2 |
| APPLICATION NO. | : 12/932793 |
| DATED | : June 30, 2015 |
| INVENTOR(S) | : Andrew Hamel et al. |

It is certified that error appears in the above-identified patent and that said Letters Patent is hereby corrected as shown below:

In the claims

Column 16, line 60, Claim 9; change "RE cutting tool" to ---RF cutting tool---.

Signed and Sealed this
First Day of December, 2015

Michelle K. Lee
*Director of the United States Patent and Trademark Office*